United States Patent
Earle et al.

(10) Patent No.: US 6,906,231 B2
(45) Date of Patent: Jun. 14, 2005

(54) AROMATIC NITRATION REACTIONS

(75) Inventors: Martyn John Earle, Belfast (GB); Suhas Prabhakar Katdare, Belfast (GB)

(73) Assignee: The Queen's University of Belfast, Belfast (GB)

(*) Notice: Subject to any disclaimer, the term of this patent is extended or adjusted under 35 U.S.C. 154(b) by 0 days.

(21) Appl. No.: 10/398,692

(22) PCT Filed: Oct. 5, 2001

(86) PCT No.: PCT/GB01/04436

§ 371 (c)(1),
(2), (4) Date: Jun. 16, 2003

(87) PCT Pub. No.: WO02/30865

PCT Pub. Date: Apr. 18, 2002

(65) Prior Publication Data

US 2004/0024266 A1 Feb. 5, 2004

(30) Foreign Application Priority Data

Oct. 10, 2000  (GB) .............................. 0024744

(51) Int. Cl.$^7$ ............................................ C07C 205/06
(52) U.S. Cl. ...................... 568/939; 568/928; 568/931; 568/940
(58) Field of Search ............................... 568/928, 931, 568/939, 940

(56) References Cited

U.S. PATENT DOCUMENTS 3,415,876 A * 12/1968 Boonstra et al. ............ 562/434
4,804,792 A *  2/1989 Mason et al. ............... 568/939
5,099,079 A *  3/1992 Quakenbush ............... 568/934

FOREIGN PATENT DOCUMENTS

EP        1 104 751 A      6/2001

OTHER PUBLICATIONS

The Merck Index, 12$^{th}$ edition, 1996, Merck & Co., Inc., Whitehouse Station, NJ, p. 1132 entry 6685.*
K.K. Laali et al., "Electophilic Nitration of Aromatics in Ionic Liquid Solvents," *J. Organic Chem.*, vol. 66, No. 1, pp. 35–40. (2001).

* cited by examiner

*Primary Examiner*—Brian Davis
(74) *Attorney, Agent, or Firm*—Drinker Biddle & Reath LLP

(57) ABSTRACT

A process for the nitration of an aromatic compound, wherein the aromatic compound is admixed with a nitrating agent in the presence of an ionic liquid is described. The method for the nitration of aromatic compounds in (e.g. neutral) ionic liquids has advantages over conventional nitrations, such as the only by-product being water, the ionic liquid not being consumed and the nitrating agent being relatively inexpensive.

14 Claims, No Drawings

AROMATIC NITRATION REACTIONS

The present invention relates to a process for the nitration of aromatic compounds.

The nitration of aromatic compounds can be achieved by a number of methods. Classically this involves the reaction of an aromatic compound with mixtures of concentrated nitric and sulfuric acids,[1] the reaction with nitronium salts such as [NO$_2$][BF$_4$],[2] and oxides of nitrogen such as NO$_2$[3], N$_2$O$_4$[4], N$_2$O$_5$,[5], HNO$_3$ with lanthanide (III) trisulflate catalysis[6] and other methods.[7]

According to one aspect of the present invention, there is provided a process for the nitration of an aromatic compound, wherein the aromatic compound is admixed with a nitrating agent in the presence of an ionic liquid.

The nitrating agent can be any suitable compound, e.g. an acid and a nitrate salt.

The method for the nitration of aromatic compounds in (e.g. neutral) ionic liquids has advantages over conventional nitrations. These are that the only by-product is water, the ionic liquid is not consumed and the nitrating agent is relatively inexpensive.

Room temperature ionic liquids have been used to great effect as solvents for a number of reactions,[8] for example Friedel-Crafts reactions,[9] isomerisations of fatty acid derivatives,[10] dimerisation reactions of alkenes,[11] Diels-Alder reactions[12] and hydrogenation reactions.[13]

Ionic liquids consist of two components, which are a positively charged cation and a negatively charged anion. Generally, any compound that meets the criteria of being a salt (consisting of an anion and cation) and is fluid at or near the reaction temperature or exits in a fluid state during any stage of the reaction may be defined as an ionic liquid.

The cation for the present process is preferably a 1-alkylpyridinium cation such as 1-hexylpyridinium. Other cations for this process are other ammonium, alkyl- or poly-alkylammonium, imidazolium, alkyl- or polyalkylimididazolium, phosphonium, alkyl- or polyalkylphosphonium, alkyloxonium, alkylsulfonium, and alkyl- or polyalkylpyrrazolium cations.

The anion for the present process is preferably a sulfur-containing anions include those based on nitrogen, phosphorous, boron, silicon, selenium, tellurium, halogens including perchlorate, oxoanions of metals, and organic anions, such as trifluoroacetate, acetate, and anions that are arsenic, antimony, and bismuth based. Other suitable anions include triflate, triflimide and methide.

More than one ionic liquid may be used.

Suitable Process Conditions

Temperature: ideally 20–80° C. but to include −40° C. to 250° C.

Pressure: ideally, atmospheric, but include 1 mbar to 100 bar

Time: ideally 24–48 hours, can be 1 minute to 1 month.

Room temperature ionic liquids such as [emim]Cl—AlCl$_3$ (X=0.67) ([emim]$^+$=1-methyl-3-ethylimidazolium cation), have also been found to been used for many reactions,[14] including nitration reactions with nitrate salts [15] and nitronium salts,[16] (although nitronium salts such as [NO$_2$][BF$_4$] are expensive and difficult to handle and chloroaluminate (III) are moisture sensitive and are eventually destroyed in the nitration reactions).

Preferably, the present invention uses of one or more water stable ionic liquids (such as these shown in FIG. 1 hereafter) as media for the reaction, and the use of nitric acid alone as the nitrating agent, as the only by-product of the reaction would be water (Scheme 1).

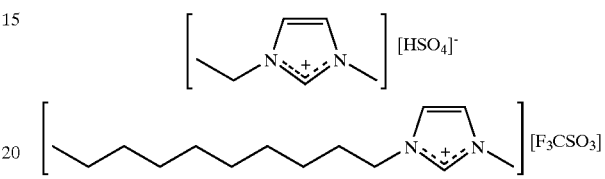

FIG. 1: The structure of the ionic liquids

[C$_2$min][HSO$_4$] and [C$_{10}$min][OTf]

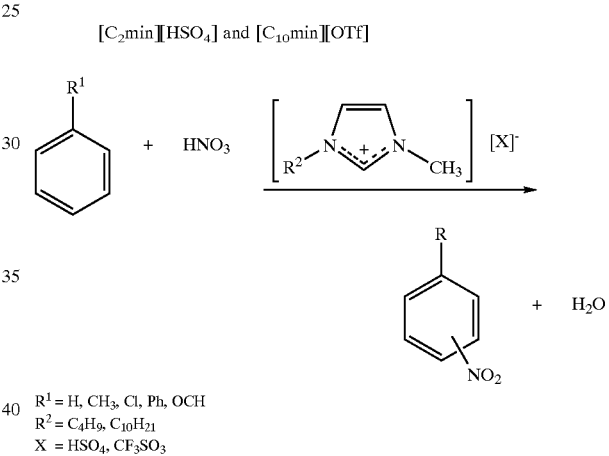

R$^1$ = H, CH$_3$, Cl, Ph, OCH
R$^2$ = C$_4$H$_9$, C$_{10}$H$_{21}$
X = HSO$_4$, CF$_3$SO$_3$

SCHEME 1

The Nitration of Aromatic Compounds with HNO$_3$

The nitration reactions of aromatic compounds using concentrated nitric acid was found to be successful in two types of ionic liquids. These were the hydrogensulfate anion and trifluoromethanesulfonate anion ionic liquids, with an imidazolium cation. The results of the nitration of benzene, chlorobenzene, toluene, biphenyl and anisole are shown in Table 1.

TABLE 1

The nitration of aromatic compounds with HNO$_3$, in ionic liquids.

| Aromatic Compound | Ionic Liquid | HNO$_3$ Conc. | Temp./° C. | Time /h. | Products (s) | % Yield |
|---|---|---|---|---|---|---|
| Benzene | [C$_{10}$mim] (OTf) | 68% | 110 | 18 h | CH$_5$-NO$_2$ | 99 |
| Chlorobenzene | [C$_4$mim] (OTf) | 68% | 130 | 18 h | 2-NO$_2$—C$_6$H$_4$Cl | 25 |
| | | | | | 3-NO$_2$—C$_6$H$_4$Cl | <1 |
| | | | | | 4-NO$_2$—C$_4$H$_4$Cl | 74 |

TABLE 1-continued

The nitration of aromatic compounds with HNO₃, in ionic liquids.

| Aromatic Compound | Ionic Liquid | HNO₃ Conc. | Temp./° C. | Time /h. | Products (s) | % Yield |
|---|---|---|---|---|---|---|
| Toluene | [C₄mim] (OTf) | 66% | 110 | 18 | 2-NO₂—C₆H₄CH₃ | 69 |
| | | | | | 3-NO₂—C₆H₄CH₃ | 2 |
| | | | | | 4-NO₂—C₆N₄CH₃ | 29 |
| Toluene | 10% [C₄mim] (OTf) | 68% | 110 | 23 | 2-NO₂—C₆H₄CH₃ | 64 |
| | | | | | 3-NO₂—C₆H₄CH₃ | 1 |
| | | | | | 4-NO₂—C₆H₄CH₃ | 35 |
| Toluene | [C₄mim] (OTf) | 100% | 110 | 120 | 2,4-(NO₂)₂-C₆Hhd 4CH₃ | 74 |
| | | | | | 2,6-(NO₂),₂-C₆H₆.CH₃ | 26 |
| Toluene | None | 68% | 110 | 25 | 2-NO₂—C₆H₄CH₃ | 40 |
| | | | | | 3-NO₂—C₆H₄CH₃ | 4 |
| | | | | | 4-NO₂—C₆H₄CH₃ | 29 |
| Toluene | [C₁₀mim] (OTf) | 68% | 110 | 18 | 2-NO₂—C₆H₄CH₃ | 50 |
| | | | | | 3-NO₂—C₆H₄Ch₃ | 3 |
| | | | | | 4-NO₂—C₆H₄CH₃ | 44 |
| Toluene | [C₂mim] (HSO₄) | 68% | 110 | 18 | 2-NO₂ —C₆H₄CH₃ | 50 |
| | | | | | 3-NO₂—C₆H₄CH₃ | 4 |
| | | | | | 4-NO₂—C₆H₄CH₃ | 45 |
| Biphenyl | [C₄mim] (OTf) | 68% | 50 | 18 | 2-nitrobiphenyl | 60 |
| | | | | | 4-nitrobiphenyl. | 34 |
| Anisole | [C₄mim] (HSO₄) | 68% | 60 | 3 | 2-NO₂—C₆H₄OCH₃ | 0 |
| | | | | | 4-NO₂—C₆H₄OCH₃ | 0 |
| Anisole | [C₄mim] (OTf) | 68% | 50 | 3 | 2-NO₂—C₆H₄OCH₃ | 35 |
| | | | | | 4-NO₂ C₆H₄OCH₃ | 65 |

The nitration of benzene proceeds smoothly to give nitrobenzene near quantitative yield, in the hydrophobic ionic liquid [C₁₀mim][OTf]. The nitration of chlorobenzene was much slower than with benzene, but gave 2- and 4-nitrochlorobenzene in excellent yield, in a 3.0:1.0 para:ortho-isomer ratio. In order to determine if the ionic liquids made a significant difference in the nitration of toluene, a control experiment was performed. This involved heating toluene and nitric acid at 110° C. for a day in the absence of ionic liquid. This gave a 67% conversion to mononitrotoluenes. The nitration of toluene with 68% HNO₃ in [C₄mim][OTf] gave 3 isomers of mononitrotoluene in quantitative yield. Quantitative dinitration was achieved by prolonged heating with 100% HNO₃.

In order to determine if the ionic liquid could be used as a catalyst, a reaction was performed with 10 mol % [C₄mim][OTf]. This gave similar results to the use of stoichiometric quantities of [C₄mim][OTf]. This means that [C₄mim][OTf] is a nitration catalyst. It is interesting to note that no trinitrotoluene was detected by this method of nitration.

By carrying the reaction out with [C₁₀mim][OTf], the effect of the hydrophobic ionic liquid was investigated. It was found that it gave similar results to the reaction carried out in [C₄mim][OTf].

A difference was observed when the reaction was carried out in [C₂mim][HSO₄]. The reactions occurred at a similar rate, but gave a higher para:ortho isomer ratio than in [C₄mim][OTf]. The nitration of biphenyl gave a maximum yield of 94% after 18 hours. If the reaction is carried out for longer, dinitrobiphenyls are formed.

The reaction of anisole with 68% nitric acid in [C₄mim][OTf] is rapid and exothermic at room temperature, so cooling of the reaction vessel is essential. A 2.0:1.0 ratio of para:ortho-nitrotoluene was obtained in 99% yield.

The range of ionic liquids that the nitration reaction succeeds is limited to those where the acid form of the anion is stronger or at least as strong as nitric acid. This favours the autoionisation (protonation of HNO₃, by NHO₃) instead of protonation of the ionic liquid anion. The protonated nitric acid [H₂NO₃]⁺ can then lose water to form the nitrating species [NO₂]⁺ A plausible mechanistic explanation is given in Scheme 2.

Scheme 2
Proposed mechanism for the nitration of aromatic in ionic liquids

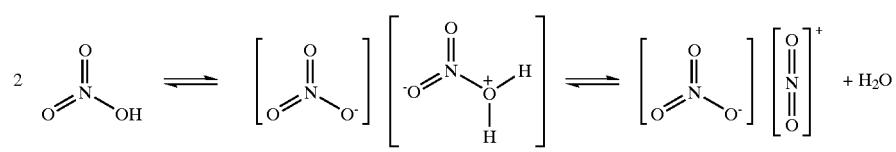

-continued

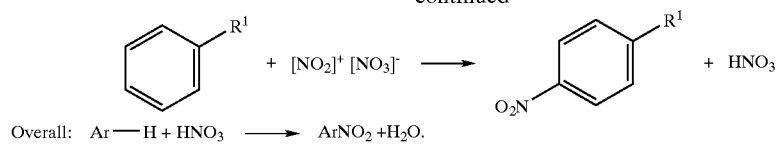

Overall: Ar—H + HNO₃ ⟶ ArNO₂ + H₂O.

The products of these reactions can be isolated in three separate ways. Vacuum distillation allows the products to be separated from this ionic liquid, which leaves the ionic liquid dried and ready for reuse, however, this cannot be used for the separation of highly nitrated products from the ionic liquid because of the high temperatures involved. Solvent extraction with cyclohexane or diethyl ether can be used to isolate most organic products from the reaction, but particularly with [C₁₀mim][OTf], it tends to leach into the organic extracting phase. The third and most successful approach is the use of steam distillation. Complete separation of the organic products from the ionic liquid can be achieved by the addition of water, followed by distillation at 120–140° C. at atmospheric pressure. The product can then be separated from the residual nitric acid usually by phase separation.

In conclusion, nitration in ionic liquids using concentrated (68%) nitric acid proceeds efficiently to give the mono-nitrated product. If 100% nitric acid is used, the di-nitrated product can be obtained. The ionic liquids could all be reused in further nitration reactions and were not destroyed, despite being in contact with nitric acid under reflux. Separation of the products was achieved by vacuum distillation, solvent extraction, or most notably, steam distillation. The only waste from these reactions is dilute nitric acid, which can be concentrated and recycle.

EP-A-1104751, filed on 21 Nov. 2000 but only published on 6 Jun. 2001, mentions nitration of naphthalene in an ionic liquid. Naphthalene is therefore not included in the definition of the aromatic compound desired for nitration as used herein.

EXAMPLE

Toluene (0.91 g, 10 mmol), 68% nitric acid (30% mmol, 2.8 g) and [C₄mim][OTf] (0.57 g, 2 mmol) and heated (oil bath at 110° C.) in a 25 ml round bottom flask equipped with a reflux condenser for 24 hours. The reaction mixture is cooled to room temperature and the nitrotoluene/residual nitric acid is distilled off at 140° C. at 1 mBar. Phase separation of the distillate yields pure nitrotoluene as a mixture of 2- and 4-isomers. The ionic liquid remains in the distillation flask and can be reused on further reactions.

The present invention also extends to the use of an ionic liquid(s) in the nitration of an aromatic compound as well as a nitrated aromatic compound whenever prepared by a process of the present invention.

REFERENCES

[1] G. A. Olah, R. Malhotra and S. C. Narang "Nitration, Methods and Mechanisms" VCH, New Your, 1989.
[2] G. A. Olah, K. K. Laali, Q. Wang, and G. K. S. Prakash, Onium Ions, Wiley, New York, 1998.
[3] H. Sato and K. Hirose, Applied Catalysis A, 1998, 174, 77–81.
[4] Iranpoor, N. H. Firouzabadi and R. Heydari, Syn. Commun. 1999, 29, 3295–3302.
[5] J. M. Bakke, I. Hegbom, E. Ovreeide, and K. Aaby, Acta Chem. Scand., 1994, 48, 1001–1006.
[6] F. J. Waller, A. G. M. Barrett, D. C. Braddock, R. M. McKinnell and D. Ramprasad, J. Chem. Soc., Perkin Trans. 1 1999, 867–871.
[7] D. W. Sheng, D. K. Joshi and M. H. Gold, Archives of Biochemistry and Biophysics, 1998, 352, 121–128.
[8] M. J. Earle and K. R. Seddon, Pure and App. Chem. 2000, in press.
[9] C. J. Adams, M. J. Earle, G. Roberts and K. R. Seddon. Chem. Commun. 1998, 2097–2098.
[10] C. J. Adams, M. J. Earle, J. Hamill, C. Lok, G. Roberts and K. R. Seddon, World Patent WO 98 07679, 1998.
[11] (a) B. Ellis, W. Keim and P. Wasserscheid, Chem. Commun. 1999, 337. (b) S. Einloft, H. Olivier and Y. Chauvin, U.S. Pat. No. 5,550,306, 1996.
[12] M. J. Earle, P. B. McCormac and K. R. Seddon, Green Chem. 1999, 1 23–25.
[13] (a) T. Fisher, A. Sethi, T. Welton, J. Woolf, Tetrahedron Lett. 1999, 40, 793–194. (b) C. J. Adams, M. J. Earle, K. R. Seddon, Chem. Commun. 1999, 1043–1044.
[14] T. Welton. Chem. Rev. 1999, 99, 2071–2083.
[15] J. A. Boon, S. W. Lander Jr., J. A. Levisky, J. L. Pflug, L. M. Skrzynecki-Cook, and J. S. Wilkes, Advances in Molten Salts, 1986, 6, 979–990.
[16] G. A. Olah, A. Orlinkov, A. B. Oxyzoglou, G. K. S. Prakash, J. Org. Chem., 1995, 60, 7348–7350.
[17] This was synthesised by the reaction of 1-decyl-3-methylimidazolium chloride (1.0 eq) and sodium trifluoromethanesulfonate (1.05 eq) in water. This resulted in the formation of a dense ionic phase, which was dissolved in dichloromethane. The dichloromethane extract was washed with deionised water, dried (MgSO₄), filtered and concentrated on a rotary evaporator.

What is claimed is:

1. A process for the nitration of an aromatic comprising admixing the aromatic compound with a nitrating agent in the presence of an ionic liquid wherein the anion of the ionic liquid is selected from the group consisting of sulfur-containing anions; halogen-containing anions; oxoanions of metals; organic anions; anions that are based on arsenic, antimony, or bismuth; triflate; triflimide; methide; and combinations thereof.

2. A process as claimed in claim 1 wherein the nitrating agent is an acid or a nitrate salt.

3. A process as claimed in claim 1 wherein the cation of the ionic liquid is selected from the group consisting of 1-alkylpyridinium, alkylammonium or poly-alkylammonium, imidazolium, alkyllimididazolium or poly-alkylimididazolium, phosphonium, alkylphosphonium or poly-alkylphosphonium, alkyloxonium, alkylsulfonium, alkylpyrrazolium, poly-alkylpyrrazolium, and combinations thereof.

4. A process as claimed in claim 3 wherein the cation is 1-hexylpyridinium.

5. A process as claimed in claim 1 wherein more than one ionic liquid is present.

6. A process as claimed in claim 1 wherein a water-stable ionic liquid is present.

7. A process as claimed in claim 1 wherein the ionic liquid is one or more of the group consisting of [C₄mim][HSO₄] and [C₁₀mim][OTf].

8. A process as claimed in claim 1 wherein the nitrating agent is nitric acid, and the ionic liquid is either a hydrogensulfate anion or a trifluoromethanesulfonate anion with an imidazolium cation.

9. A process as claimed in claim 1 which selectively forms a mono or di-nitrated product.

10. A process as claimed in claim 1 wherein the reaction products are isolated by one or more of vacuum distillation, solvent extraction and steam distillation.

11. A process as claimed in claim 1 wherein the aromatic compound is benzene, chlorobenzene, toluene, biphenyl or anisole.

12. The process as claimed in claim 1 wherein the anion is based on nitrogen, phosphorous, boron silicon, selenium, or tellurium.

13. The process as claimed in claim 1 wherein the halogen containing anion is a perchlorate.

14. The process as claimed in claim 1 wherein the organic anion is trifluoroacetate or acetate.

* * * * *